(12) United States Patent
Kim et al.

(10) Patent No.: US 10,245,442 B2
(45) Date of Patent: Apr. 2, 2019

(54) APPARATUS FOR RELAXING RESPIRATORY TRACT AND BRONCHIAL TUBE

(71) Applicant: COLOR SEVEN CO., LTD., Seoul (KR)

(72) Inventors: Nam Gyun Kim, Seoul (KR); Kyong Jun Park, Seoul (KR)

(73) Assignee: COLOR SEVEN CO., LTD., Seoul (KR)

( * ) Notice: Subject to any disclaimer, the term of this patent is extended or adjusted under 35 U.S.C. 154(b) by 49 days.

(21) Appl. No.: 15/103,095

(22) PCT Filed: Dec. 4, 2014

(86) PCT No.: PCT/KR2014/011840
§ 371 (c)(1),
(2) Date: Jun. 9, 2016

(87) PCT Pub. No.: WO2015/093761
PCT Pub. Date: Jun. 25, 2015

(65) Prior Publication Data
US 2016/0375265 A1 Dec. 29, 2016

(30) Foreign Application Priority Data
Dec. 16, 2013 (KR) .................. 10-2013-0156384

(51) Int. Cl.
*A61N 5/06* (2006.01)
*A61H 39/04* (2006.01)
*A61N 5/067* (2006.01)

(52) U.S. Cl.
CPC ........... *A61N 5/0613* (2013.01); *A61H 39/04* (2013.01); *A61H 2201/10* (2013.01);
(Continued)

(58) Field of Classification Search
CPC .......... A61N 5/0613; A61N 2005/0626; A61N 2005/067; A61N 2005/0651;
(Continued)

(56) References Cited

U.S. PATENT DOCUMENTS

2011/0106224 A1* 5/2011 Kribbe ................ A61N 5/0613
607/91
2012/0253236 A1* 10/2012 Snow .................. A61N 5/0618
601/2

FOREIGN PATENT DOCUMENTS

KR         20-0233007 Y1    9/2001
KR     10-2009-0099914 A    9/2009
(Continued)

Primary Examiner — Rex R Holmes
(74) Attorney, Agent, or Firm — Weiss & Moy, P.C.; Jeffrey D. Moy

(57) ABSTRACT

The present invention relates to an apparatus for relaxing a respiratory tract and a bronchial tube, wherein the apparatus is manufactured in a form of a necklace hung on the neck, and a color light in the visible light wavelength band is irradiated at the region of the Tiantu point, which is known to be useful for the prevention and treatment of human respiratory diseases, that is, a dent region at which ends of left and right clavicle meet each other below the front of the neck, for a predetermined time to induce the secretion of a material for relaxing muscles (e.g., nitrogen monoxide or the like) in muscular cells of the respiratory tract and the bronchial tube, thereby relaxing the respiratory tract and the bronchial tube.

12 Claims, 4 Drawing Sheets

(52) U.S. Cl.
CPC ............... *A61H 2201/165* (2013.01); *A61H 2201/1609* (2013.01); *A61H 2201/501* (2013.01); *A61H 2201/5048* (2013.01); *A61H 2201/5092* (2013.01); *A61H 2201/5097* (2013.01); *A61N 2005/067* (2013.01); *A61N 2005/0626* (2013.01); *A61N 2005/0645* (2013.01); *A61N 2005/0651* (2013.01); *A61N 2005/0653* (2013.01); *A61N 2005/0663* (2013.01)

(58) Field of Classification Search
CPC .... A61N 2005/0653; A61N 2005/0645; A61N 2005/0663; A61M 21/00; A61H 39/04; A61H 2201/501; A61H 2201/10; A61H 2201/5048; A61H 2201/16
See application file for complete search history.

(56) References Cited

FOREIGN PATENT DOCUMENTS

| | | |
|---|---|---|
| KR | 10-1039636 B1 | 6/2011 |
| KR | 10-1157457 B1 | 6/2012 |
| KR | 10-2013-0068754 A | 6/2016 |

\* cited by examiner

APPARATUS FOR RELAXING RESPIRATORY TRACT AND BRONCHIAL TUBE

TECHNICAL FIELD

The present invention relates to an apparatus for relaxing a respiratory tract and a bronchial tube, and more particularly, to an apparatus for relaxing a respiratory tract and a bronchial tube manufactured in a necklace shape.

BACKGROUND ART

Relaxation of a respiratory tract or a bronchial tube is very important for prevention or treatment of human respiratory diseases. When the respiratory tract or the bronchial tube is contracted, symptoms such as cough, bronchial inflammation, asthma, and chronic obstructive pulmonary disease may be induced.

Meanwhile, although there are methods to relax a respiratory tract or a bronchial tube of directly taking medicine or inhaling medicine using an auxiliary device (for example, a respirator and the like for inhalation of fine powder that is usable for treatment of respiratory tract diseases described in a patent document 1 (KR10-2003-0062271 A)), a problem is that there are various side effects due to the medicine.

On the other hand, apparatuses have been developed that stimulates the vagus nerve by electrically stimulating a part of a neck and relaxes muscles of respiratory tract wall using adrenalin secreted from the vagus nerve for relaxing the respiratory tract or the bronchial tube.

However, although the apparatus for stimulating the vagus nerve of a neck portion makes breathing easy by relaxing the respiratory tract or the bronchial tube, the apparatus is inconvenient for a person sensitive to an electrical stimulation and is particularly inconvenient for an individual to use the apparatus while holding in hands since it takes at least 20 to 30 minutes to induce secretion of a material (for example, the above-described adrenaline) that relaxes the respiratory tract or the bronchial tube.

DISCLOSURE

Technical Problem

Therefore, the applicant (or the inventor) developed an apparatus for relaxing a respiratory tract and a bronchial tube that may resolve the above-described problems of the conventional method or apparatus for relaxing the respiratory tract or the bronchial tube and is inexpensive and convenient to use anywhere and anytime.

The present invention is directed to providing an apparatus for relaxing a respiratory tract and a bronchial tube that is manufactured in a necklace shape for wearing around a neck, irradiates a recessed portion known as a tiantu point below the front of the neck at which ends of left and right clavicles meet each other and is known to be useful for prevention and treatment of human respiratory diseases with color light of a visible light wavelength band for a predetermined duration on, and induces muscle cells of the respiratory tract and the bronchial tube to secrete a material that relaxes the muscles (for example, nitric oxide and the like) to relax the respiratory tract and the bronchial tube.

Technical Solution

One aspect of the present invention provides an apparatus for relaxing a respiratory tract and bronchial tube including a color light therapy device that relaxes a respiratory tract and a bronchial tube by emitting color light in a wavelength band of visible light through a color light emitting protrusion formed protruding from a rear surface of the body and accommodated in a recessed portion at which ends of left and right clavicles meet each other below the front of the neck for a predetermined duration with a predetermined emitting pattern and inducing muscle cells of the respiratory tract and the bronchial tube to secrete a material that relaxes the muscles when an operation button installed on a front surface of a body is pushed and an operation of the color light therapy device is started; and a pair of neck bends that extend from both side surfaces of the color light therapy device, elastically gird a perimeter of a user's neck, and have two ends at which pressing protrusions that press the rear of the user's neck while being fixed to the rear of the user's neck.

The color light therapy device may further include a vibration detection signal generator that is installed inside the body and, when an operation of the color light therapy device signal is finished and a vibration detector exposed from the rear surface of the body detects vibrations (for example, vibrations due to cough of a user) greater than a predetermined reference value, outputs a vibration detection signal to transmit the vibration detection signal to the controller, and accordingly, the controller may output a color light emitting signal for emitting color light for a predetermined duration with a predetermined emitting pattern according to the vibration detection signal.

The color light therapy device may further include a sound detection signal generator that is installed inside the body and, when an operation of the color light therapy device is finished, and a sound detector exposed from a rear surface of the body detects a sound (for example, sound due to a cough of a user) with a volume greater than a predetermined reference value, outputs a sound detection signal to transmit the sound detection signal to the controller, and accordingly, the controller may output a color light emitting signal for emitting color light for a predetermined duration with a predetermined emitting pattern according to the sound detection signal.

The color light therapy device may further include a wireless transceiver that is installed inside the body, receives the operation start signal or the operation end signal from an external remote controller (for example, a personal computer (PC), a notebook, a tablet, a smartphone, a personal digital assistant (PDA)) allowed to wirelessly communicate using a wireless communication method such as radio frequency (RF), Bluetooth, and ZigBee methods, and transmits the operation start signal or the operation end signal to the controller.

Advantageous Effects

In an apparatus for relaxing a respiratory tract and a bronchial tube according to an exemplary embodiment of the present invention, since the apparatus manufactured in a necklace shape and relaxes a respiratory tract or a bronchial tube using visible light harmless to a human body, the apparatus can be inexpensive, conveniently usable anywhere and anytime, thus prevent a contraction of the respiratory tract or the bronchial tube that is important in alleviating symptoms such as cough, bronchial inflammation, asthma, and chronic obstructive pulmonary disease, and be particularly very useful for sports players for whom taking medicine can be problematic due to drug tests or for users (for example, children) who are uneasy about side effects of a medication.

MODES OF THE INVENTION

Figure 1:
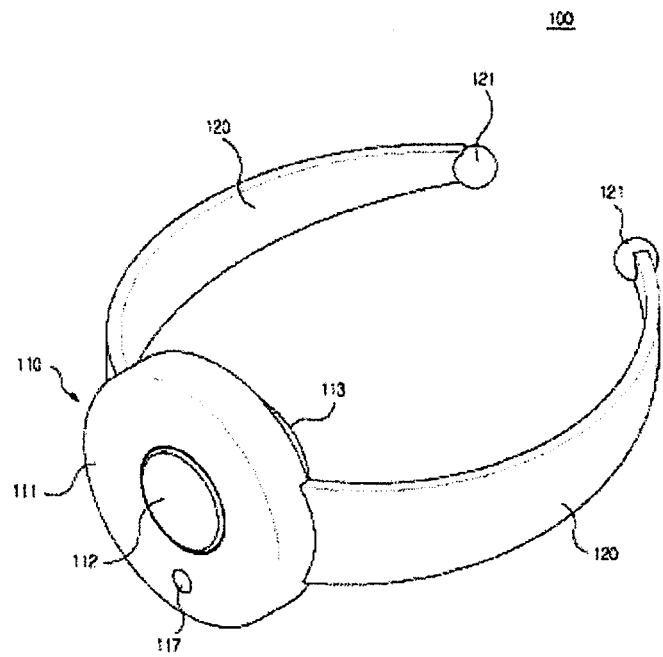
FIG. 1 is a perspective view illustrating the front of an apparatus for relaxing a respiratory tract and a bronchial tube according to an embodiment of the present invention.
Figure 2:
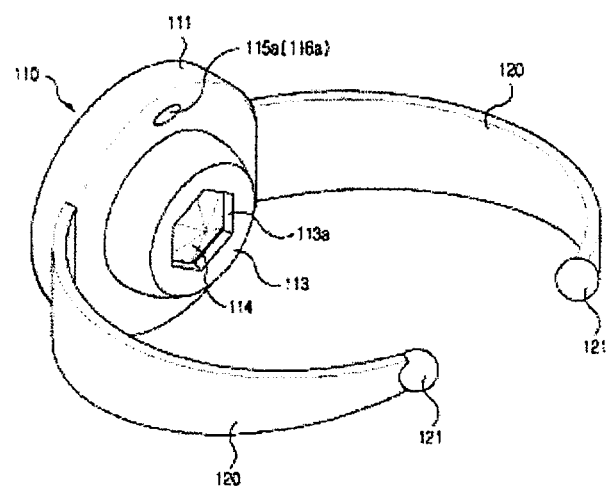
FIG. 2 is a perspective view illustrating the rear of the apparatus for relaxing a respiratory tract and a bronchial tube according to the embodiment of the present invention.
Figure 3:
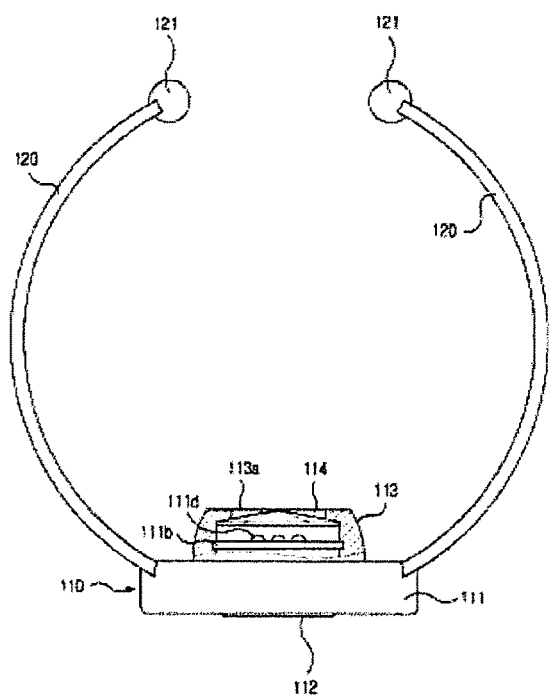
FIG. 3 is a planar and partial cross-sectional view illustrating the apparatus for relaxing a respiratory tract and a bronchial tube according to the embodiment of the present invention.
Figure 4:
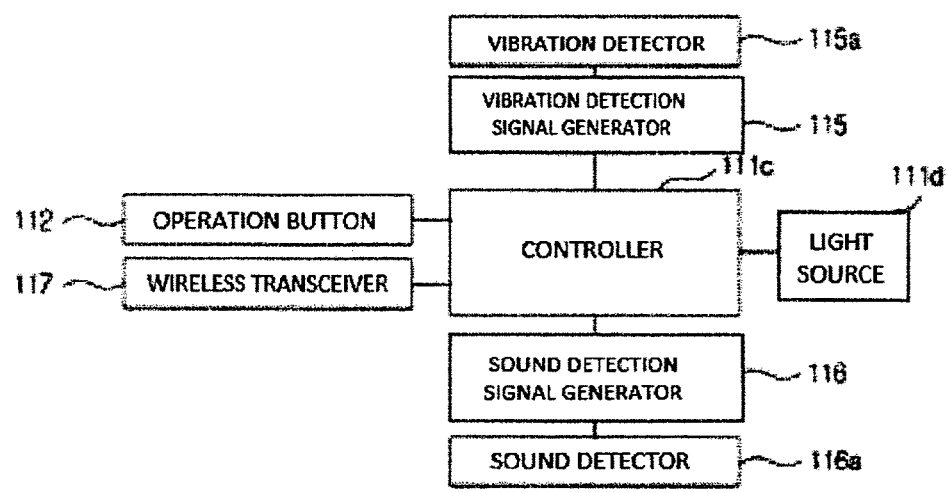
FIG. 4 is a block diagram of an electronic device for the apparatus for relaxing a respiratory tract and a bronchial tube according to the embodiment of the present invention.

Hereinafter, an embodiment of the present invention will be described in detail with reference to the accompanying drawings.

Referring to FIGS. 1 to 4, an apparatus for relaxing a respiratory tract and a bronchial tube 100 according to the embodiment of the present invention is manufactured in a necklace shape and has distinguishable parts consisting of a color light therapy device 110 and a pair of neck bends 120.

When an operation button 112 installed on a front surface of the body 111 is pushed and an operation of the color light therapy device 110 is started, the color light therapy device 110 emits color light in a visible light wavelength band for a predetermined duration with a predetermined emitting pattern through a color light emitting protrusion 113 formed protruding from a rear surface of the body 111 accommodated in a recessed portion below the front of the neck at which ends of left and right clavicles meet each other and induces muscle cells of a respiratory tract and a bronchial tube to secrete a material that relaxes the muscles (for example, nitric oxide and the like) to relax the respiratory tract and the bronchial tube.

The pair of neck bends 120 extend from both side surfaces of the body 111 of the color light therapy device 110, and a battery 111a and a printed circuit board (PCB) 111b are installed inside the body 111. A controller 111c that outputs a color light emitting signal for emitting color light for a predetermined duration with a predetermined emitting pattern according to an operation start signal and at least one of a light emitting diode (LED), an organic LED (OLED), a laser diode (LD), and a three color LED capable of generating various color light as a light source 111d that is turned on according to the color light emitting signal and emits color light in a visible light wavelength band for relaxing a respiratory tract and a bronchial tube are mounted on the PCB 111b.

The battery 111a is a single-use battery that is usable only once or a rechargeable battery that may be reused when charged, and the rechargeable battery receives recharging power through a recharging adaptor connected to a recharging terminal (not shown) disposed on one surface of the body 111.

Note that a method of recharging the rechargeable battery may be implemented by a contact recharging method in which a recharging terminal is connected to a recharger by being in contact with each other and may also be implemented by various wireless recharging methods such as a wireless recharging method using electromagnetic induction, a magnetic (magnetic field) resonance method, an electric field resonance method, a radio wave method using a micro wave or the like.

In the embodiment according to the present invention, it is preferable that the controller 111c output a color light emitting signal for emitting color light in any one of emitting patterns of color light classified as continuous emitting and discontinuous emitting for 1 to 60 minutes (preferably, for 10 to 20 minutes) wherein the color light has an intensity in the range of 1 to 50 mW/cm$^2$ (preferably, in the range of 8 to 10 mW/cm$^2$) and is in a visible light wavelength band in the range of 400 to 1000 nm (preferably, a visible light wavelength band in the range of 450 to 480 nm).

When the controller 111c outputs a color light emitting signal for emitting color light for the color light emitting duration with the color light emitting pattern, with the intensity of the light, and in the wavelength band as described above, secretion of a material that relaxes a respiratory tract of a bronchial tube is sufficiently induced as a result by the color light with which a recessed portion known as a tiantu point below the front of the neck at which ends of left and right clavicles meet each other and is known to be useful for prevention and treatment of human respiratory diseases is irradiated.

The operation button 112 of the color light therapy device 110 is installed on a front surface the body 111 and alternately outputs an operation start signal and an operation end signal every time the operation button 112 is pushed.

The color light emitting protrusion 113 of the color light therapy device 110 is formed protruding from a rear surface of the body 111 and has a leading end in which a light emitting port 113a is formed for concentrating color light from the light source 111d and emitting the concentrated color light to the outside.

A light filter 114 of the color light therapy device 110 is installed inside the color light emitting protrusion 113, filters and focuses color light emitted from the light source 111d, and emits the color light through the light emitting port 113a.

It is preferable that the light filter 114 be made of plastic, glass, quartz, crystal, crystal glass, or the like, and a transmitting surface through which color light transmits be processed by cutting into a circular or polygonal shape or have a planar or convex lens-like shape.

A vibration detection signal generator 115 of the color light therapy device 110 is installed inside the body 111, outputs a vibration detection signal, and transmits the vibration detection signal to the controller 111c when the operation end signal is output, that is, when the color light therapy device 110 does not emit color light and a vibration detector 115a exposed from the rear surface of the body 111 detects vibrations greater than a predetermined reference value. Accordingly, the controller 111c outputs a color light emitting signal for emitting color light for a predetermined duration with a predetermined emitting pattern according to the vibration detection signal.

A sound detection signal generator 116 of the color light therapy device 110 is installed inside the body 111, outputs a sound detection signal, and transmits the sound detection signal to the controller 111c when the operation end signal is output, that is, when the color light therapy device 110 does not emit color light and a sound detector 116a exposed from the rear surface of the body 111 detects a sound with a volume greater than a predetermined reference value. Accordingly, the controller 111c outputs a color light emitting signal for emitting color light for a predetermined duration with a predetermined emitting pattern according to the sound detection signal.

A wireless transceiver 117 of the color light therapy device 110 is installed inside the body 111, receives the operation start signal or the operation end signal from an external remote controller 200 capable of wireless communication using a wireless communication method such as radio frequency (RF), Bluetooth, and ZigBee methods, and transmits the operation start signal or the operation end signal to the controller 111c.

The remote controller 200 is a portable smart communications device including programs with which a user may control an operation of a color light therapy device through a user interface (UI) screen, for example, a personal computer (PC), a notebook, a tablet, a smartphone, a personal digital assistant (PDA), or the like.

The pair of neck bends 120 extend from both side surfaces of the color light therapy device 110, elastically gird a perimeter of a user's neck, and have two ends at which pressing protrusions 121 that press the rear of the user's neck and are fixed to the rear of the user's neck.

The length of the pair of neck bends 120 may be manufactured to be adjustable, and a structure for length changing may be implemented in various forms by those skilled in the art. For example, a sliding method applied to a conventional head set may be adopted for the structure for length adjustment.

The apparatus for relaxing a respiratory tract and a bronchial tube 100 according to the embodiment of the present invention described as above is used as follows.

Figure 5:
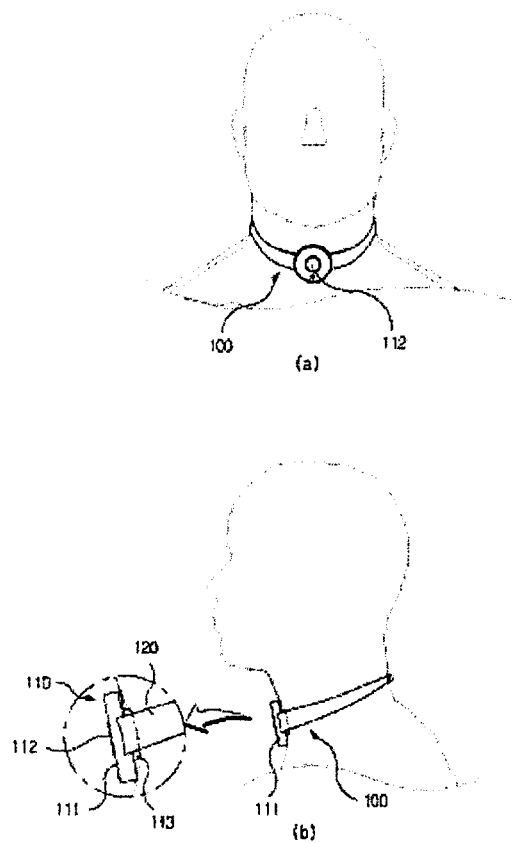
FIG. 5 is a view of the apparatus for relaxing a respiratory tract and bronchial tube according to the embodiment of the present invention worn around a neck and being used.

FIG. 5 is a view of the apparatus for relaxing a respiratory tract and a bronchial tube 100 according to the embodiment of the present invention worn around a neck and being used, FIG. 5A is a front view of a user using the apparatus, and FIG. 5B is a side view of the user using the apparatus.

As illustrated in FIG. 5B, a user wears the apparatus for relaxing a respiratory tract and bronchial tube 100 around the neck by pressing the color light emitting protrusion 113 against a recessed portion below the front of the neck at which ends of left and right clavicles meet each other so that the color light emitting protrusion 113 is accommodated in the recessed portion. At this point, it is preferable that a user only moderately press the color light emitting protrusion 113 and not feel pain caused by excessive pressing of the color light emitting protrusion 113 against the recessed portion of the neck.

Accordingly, when a user presses the color light emitting protrusion 113 against the recessed portion so that the color light emitting protrusion 113 is accommodated in the recessed portion, color light emitted from the light source 111d relatively may not leak away therefrom, the recessed portion is maximally irradiated, and thus, an effect of relaxing of a respiratory tract or a bronchial tube can be maximized as compared to when the color light emitting protrusion 113 is separated from the recessed portion and the recessed portion is irradiated with the color light.

When a user wears the apparatus for relaxing a respiratory tract and a bronchial tube 100 made in a necklace shape around a neck and pushes the operation button 112, the operation start signal is transmitted to the controller 111c.

Then, the controller 111c outputs a color light emitting signal for emitting color light for a predetermined duration with a predetermined emitting pattern. For example, the controller 111c outputs a color light emitting signal for emitting color light in any one of emitting patterns of color light classified as continuous emitting and discontinuous emitting for 10 to 60 minutes, wherein the color light has an intensity in the range of 8 to 10 $mW/cm^2$ and is of a wavelength band of visible light in the range of 450 to 480 nm.

When the color light emitting signal is transmitted to the light source 111d, the light source 111d turns on and emits color light in a wavelength band of visible light for relaxing a respiratory tract and a bronchial tube, and the color light emitted from the light source 111d passes through the light filter 114 installed inside the color light emitting protrusion 113 to then exit through the light emitting port 113a and be concentrated on a recessed portion at which the ends of the left and right clavicles meet each other below the front of the neck that is known to be useful for prevention and treatment of human respiratory diseases and is known as the tiantu point.

As described above, the color light emitted to the recessed portion of the user's neck induces muscle cells of the respiratory tract and the bronchial tube to secrete a material that relaxes the muscles and thus relaxes the respiratory tract and the bronchial tube.

For example, color light with which the recessed portion of the user's neck is irradiated generates cyclic adenosine monophosphate (cAMP) or secretes nitric oxide by acting on light acceptors of tissue cells of a respiratory tract or a bronchial tube, activates guanylate cyclase in the tissue cells, increases concentration of cyclic guanosine monophosphate (cGMP), and thus, relaxes the respiratory tract or the bronchial tube.

As known from the above description, since the apparatus for relaxing a respiratory tract and a bronchial tube is manufactured in a necklace shape and relaxes a respiratory tract or a bronchial tube using visible light harmless to a human body, the apparatus can be inexpensive, conveniently used anywhere and anytime, thus, prevent the contraction of the respiratory tract or the bronchial tube that is important to alleviate symptoms, such as cough, bronchial inflammation, asthma, and chronic obstructive pulmonary disease, and particularly, is very useful for sports players for whom take drugs is problematic due to drug tests or users (for example, children) who are uneasy about side effects of medication.

Meanwhile, when a predetermined time has elapsed, the controller 111c automatically turns the light source 111d off and finishes a color light emitting operation.

Alternatively, a user may finish a color light emitting operation of the light source 111d by pushing the operation button 112 again and transmitting an operation end signal to the controller 111c while the color light emitting operation of the light source 111d is in progress.

On the other hand, while a user is wearing the apparatus for relaxing a respiratory tract and bronchial tube 100 made in a necklace shape around a neck, when color light emitting operation of the light source 111d is finished as described above and the user coughs, the color light therapy device 110 automatically starts a color light emitting operation.

For example, as described above, when the user coughs and the vibration detector 115a exposed on a rear surface of body 111 of the color light therapy device 110 detects vibrations greater than a predetermined reference value, the vibration detection signal generator 115 outputs a vibration detection signal and transmits the vibration detection signal to the controller 111*c*.

Accordingly, the controller 111*c* outputs a color light emitting signal for emitting color light for a predetermined duration with a predetermined emitting pattern according to the vibration detection signal. A color light emitting operation of the light source 111*d* after the color light emitting signal is output is the same as the color light emitting operation described with reference to FIG. 5.

In addition, for example, when a user coughs as described above, and the sound detector 116*a* exposed on the rear surface of body 111 of the color light therapy device 110 detects sound with a volume greater than a predetermined reference value, the sound detection signal generator 116 outputs a sound detection signal and transmits the sound detection signal to the controller 111*c*.

Accordingly, the controller 111*c* outputs a color light emitting signal for emitting color light for a predetermined duration with a predetermined emitting pattern according to the sound detection signal. A color light emitting operation of the light source 111*d* after the color light emitting signal is output is the same as the color light emitting operation described with reference to FIG. 5.

Figure 6:
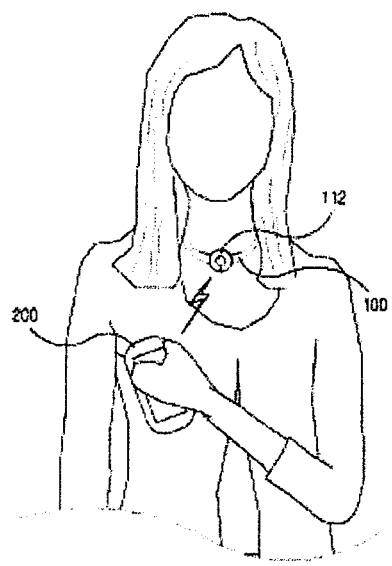
FIG. 6 is a view of the apparatus for relaxing a respiratory tract and a bronchial tube according to the embodiment of the present invention worn around a neck and an operation of the apparatus being controlled by a smartphone.

FIG. 6 is a view of the apparatus for relaxing a respiratory tract and a bronchial tube 100 according to the embodiment of the present invention worn around a neck and being controlled and used by the remote controller 200, for example, a smartphone.

In this case, the controller 111*c* of the color light therapy device 110 receives the operation start signal or the operation end signal from the external remote controller 200 capable of wireless communication using a wireless communications method such as RF, Bluetooth, and ZigBee methods through the wireless transceiver 117.

When the controller 111*c* receives the operation start signal from the external remote controller 200, the controller 111*c* outputs a color light emitting signal for emitting color light for a predetermined duration with a predetermined emitting pattern. A color light emitting operation of the light source 111*d* after the color light emitting signal is output is the same as the color light emitting operation described with reference to FIG. 5.

In addition, when a predetermined time has elapsed, the controller 111*e* automatically turns the light source 111*d* off and finishes the color light emitting operation.

When the controller 111*c* receives the operation end signal from the external remote controller 200, the controller 111*c* may finish a color light emitting operation of the light source 111*d* while the color light emitting operation of the light source 111*d* is in progress.

In this case, a user may also finish a color light emitting operation of the light source 111*d* by pushing the operation button 112 and transmitting an operation end signal to controller 111*c* during the color light emitting operation of the light source 111*d*.

The above-described apparatus for relaxing a respiratory tract and a bronchial tube according to the embodiment of the present invention is not limited to the above-described embodiments, and the spirit of the invention ranges to a scope in which those skilled in the art may variously change without departing from the gist of the present invention claimed by the appended claims.

The invention claimed is:

1. A necklace shape apparatus for treating a respiratory ailment, comprising:

a color light therapy device (110) that relaxes a treatment area by emitting color light in a wavelength band of visible light through a color light emitting protrusion (113) formed protruding from a rear surface of a body (111) and positioned in a front of the treatment area for a predetermined duration with a predetermined emitting pattern and causing the treatment area to secrete a material that relaxes the treatment area when an operation button (112) installed on a front surface of the body (111) is pushed and an operation of the color light therapy device (110) is started; and a pair of neck bends (120) that extend from both side surfaces of the color light therapy device (110), elastically gird a perimeter above the treatment area allowing the rear surface of the body (111) to be placed in front of the treatment area, and having two ends at which pressing protrusions (121) press against an area above and behind the treatment area, wherein the pair of neck bends (120) extend from the both side surfaces of the color light therapy device (110), and a battery (111*a*) and a printed circuit board (PCB) (111*b*) are installed inside the color light therapy device (110), and wherein the color light therapy device (110) comprises:

the body (111) in which a controller (111*c*) that outputs a color light emitting signal for emitting color light for a predetermined duration with a predetermined emitting pattern according to an operation start signal and at least one of any one of a light emitting diode (LED), an organic LED (OLED), a laser diode (LD), and a three color LED that is allowed to generate various color light as a light source (111*d*) that is turned on according to the color light emitting signal and emits color light of a wavelength band of visible light for relaxing the treatment area are mounted on the PCB (111*b*);

an operation button (112) that is installed on the front surface of the body (111) and alternately outputs an operation start signal and an operation end signal every time the operation button (112) is pushed;

the color light emitting protrusion (113) protruding from the rear surface of the body (111) and has a leading end in which a light emitting port (113*a*) is formed for concentrating color light emitted from the light source (111*d*) and emitting the concentrated color light to the outside;

a light filter (114) that is installed inside the color light emitting protrusion (113), filters and focuses color light emitted from the light source (111*d*) and emits the color light through the light emitting port (113*a*); and a vibration detection signal generator (115) that is installed inside the body (111) and, when the operation end signal is output and a vibration detector (115*a*) exposed from the rear surface of the body (111) detects vibrations greater than a predetermined reference value, outputs a vibration detection signal to transmit the vibration detection signal to the controller (111*c*).

2. The necklace shape apparatus of claim 1, wherein the controller (111*c*) outputs the color light emitting signal for emitting color light for the predetermined duration with the predetermined emitting pattern according to the vibration detection signal.

3. The apparatus of claim 1, wherein the color light therapy device (110) further includes a wireless transceiver (117) that is installed inside the body (111), receives the operation start signal or the operation end signal from an external remote controller (200) allowed to wirelessly communicate using a wireless communication method such as radio frequency (RF), Bluetooth, and ZigBee methods, and transmits the operation start signal or the operation end signal to the controller (111c).

4. The necklace shape apparatus of claim 3, wherein the remote controller (200) includes a portable smart communication device including programs with which a user controls an operation of the color light therapy device through a user interface (UI) screen.

5. The necklace shape apparatus of claim 1, wherein the light filter (114) is formed of any one of plastic, glass, quartz, crystal, and crystal glass, and a transmitting surface through which color light transmits is processed by cutting in a circular or polygonal shape or has a planar or convex lens-like shape.

6. The apparatus of claim 1, wherein the controller (111c) outputs the color light emitting signal for emitting color light in any one of emitting patterns of color light classified as continuous emitting and discontinuous emitting for 1 to 60 minutes, wherein the color light has an intensity in the range of 1 to 50 $mW/cm^2$ and is of a wavelength band of visible light in the range of 400 to 1000 nm.

7. A necklace shape apparatus for treating a respiratory ailment, comprising:
a color light therapy device (110) that relaxes a treatment area by emitting color light in a wavelength band of visible light through a color light emitting protrusion (113) formed protruding from a rear surface of a body (111) and positioned in a front of the treatment area for a predetermined duration with a predetermined emitting pattern and causing the treatment area to secrete a material that relaxes the treatment area when an operation button (112) installed on a front surface of the body (111) is pushed and an operation of the color light therapy device (110) is started; and
a pair of neck bends (120) that extend from both side surfaces of the color light therapy device (110), elastically gird a perimeter above the treatment area allowing the rear surface of the body (111) to be placed in front of the treatment area, and having two ends at which pressing protrusions (121) press against an area above and behind the treatment area, wherein the pair of neck bends (120) extend from the both side surfaces of the color light therapy device (110), and a battery (111a) and a printed circuit board (PCB) (111b) are installed inside the color light therapy device (110), and wherein the color light therapy device (110) includes:
the body (111) in which a controller (111c) that outputs a color light emitting, signal for emitting color light for a predetermined duration with a predetermined emitting pattern according to an operation start signal and at least one of any one of a light emitting diode (LED), an organic LED (OLED), a laser diode (LD), and a three color LED that is allowed to generate various color light as a light source (111d) that is turned on according to the color light emitting signal and emits color light of a wavelength band of visible light for relaxing the treatment area are mounted on the PCB (111b);
an operation button (112) that is installed on the front surface of the body (111) and alternately outputs an operation start signal and an operation end signal every time the operation button (112) is pushed;
the color light emitting protrusion (113) protruding from the rear surface of the body (111) and has a leading end in which a light emitting port (113a) is formed for concentrating color light emitted from the light source (111d) and emitting the concentrated color light to the outside;
a light filter (114) that is installed inside the color light emitting protrusion (113), filters and focuses color light emitted from the light source (111d) and emits the color light through the light emitting port (113a); and
a sound detection signal generator (116) that is installed inside the body (111) and, when the operation end signal is output, and a sound detector (116a) exposed from the rear surface of the body (111) detects a sound with a volume greater than a predetermined reference value, outputs a sound detection signal to transmit the sound detection signal to the controller (111c).

8. The necklace shape apparatus of claim 7, wherein the controller (111c) outputs the color light emitting signal for emitting color light for the predetermined duration with the predetermined emitting pattern according to the sound detection signal.

9. The apparatus of claim 7, wherein the color light therapy device (110) further includes a wireless transceiver (117) that is installed inside the body (111), receives the operation start signal or the operation end signal from an external remote controller (200) allowed to wirelessly communicate using a wireless communication method such as radio frequency (RF), Bluetooth, and ZigBee methods, and transmits the operation start signal or the operation end signal to the controller (111c).

10. The necklace shape apparatus of claim 9, wherein the remote controller (200) includes a portable smart communication device including programs with which a user controls an operation of the color light therapy device through a user interface (UI) screen.

11. The necklace shape apparatus of claim 7, wherein the light filter (114) is formed of any one of plastic, glass, quartz, crystal, and crystal glass, and a transmitting surface through which color light transmits is processed by cutting in a circular or polygonal shape or has a planar or convex lens-like shape.

12. The apparatus of claim 7, wherein the controller (111c) outputs the color light emitting signal for emitting color light in any one of emitting patterns of color light classified as continuous emitting and discontinuous emitting for 1 to 60 minutes, wherein the color light has an intensity in the range of 1 to 50 $mW/cm^2$ and is of a wavelength band of visible light in the range of 400 to 1000 nm.

* * * * *